United States Patent [19]

Paulus et al.

[11] 4,049,807
[45] Sept. 20, 1977

[54] 2-AMINO-1,3-THIAZINES THEIR USE AND PREPARATION

[75] Inventors: Wilfried Paulus, Krefeld; Hans Scheinpflug, Leverkusen; Hermann Genth, Krefeld, all of Germany

[73] Assignee: Bayer Aktiengesellschaft, Leverkusen, Germany

[21] Appl. No.: 581,526

[22] Filed: May 28, 1975

[30] Foreign Application Priority Data

June 1, 1974 Germany .............................. 2426653

[51] Int. Cl.² ...................... C07D 279/06; A01N 9/12
[52] U.S. Cl. ....................................... 424/246; 544/55; 544/53
[58] Field of Search ...................... 260/243 R; 424/246

[56] References Cited

U.S. PATENT DOCUMENTS 3,228,935  1/1966  Behner et al. ........................ 260/243

FOREIGN PATENT DOCUMENTS 1,159,953  12/1963  Germany .............................. 260/243

*Primary Examiner*—John M. Ford
*Attorney, Agent, or Firm*—Burgess, Dinklage & Sprung

[57] ABSTRACT 2-amino-1,3-thiazines having the formula

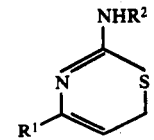

wherein
 $R^1$ is optionally substituted carbocyclic or heterocyclic aromatic and
 $R^2$ is hydrogen, alkyl, alkenyl or optionally substituted substituted carbocyclic aromatic.

The 2-amino-1,3-thiazines are useful for combatting fungi and bacteria, for example, in plant protection for combatting archimycetes, phycomycetes and the like, are prepared by reacting beta-halogeno-ethyl-ketone having the formula

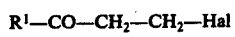

wherein
 Hal is halogen and
 $R^1$ is as defined above, with thiourea of the general formula

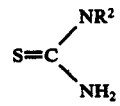

wherein
 $R^2$ is as defined above.

33 Claims, No Drawings

2-AMINO-1,3-THIAZINES THEIR USE AND PREPARATION

This invention relates to derivatives of 2-amino-1,3-thiazine as well as to their production and use.

SUMMARY

It has been found that derivatives of 2-amino-1,3-thiazine of the formula

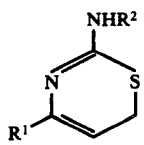

(I)

wherein
R¹ represents an optionally substituted carbocyclic or heterocyclic aromatic radical and
R² represents hydrogen, an alkyl, alkenyl or optionally substituted carbocyclic aromatic radical
and addition salts thereof. The compounds of the invention (i.e. compounds of the formula (I) and addition salts thereof) may be prepared by reacting a,β-halogenoethyl-ketone of the formula

(II)

wherein
Hal represents halogen and
R¹ has the abovementioned meaning
is reacted with a thiourea of the formula

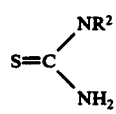

(III)

wherein
R² has the abovementioned meaning.

DESCRIPTION

In general, the reaction is performed at temperatures ranging from 15° to 150° C, preferably 40° to 110° C.

Suitable alkyl and alkenyl groups are straight-chain or branched alkyl and alkenyl radicals with up to 18, preferably up to 12, in particular up to 6 carbon atoms; by way of example there may be mentioned: methyl, ethyl, propyl, isopropyl, butyl, isobutyl, tert.-butylamyl, isoamyl, hexyl, heptyl, nonyl, decyl, undecyl and dodecyl radicals; possible alkenyl radicals are for example: vinyl, allyl, isopropenyl, butenyl, isobutenyl, pentenyl and hexenyl. Alkyl and alkenyl radicals with up to 3 carbon atoms are particularly preferred, namely: methyl, ethyl, propyl, isopropyl, vinyl, allyl.

Suitable carbocyclic aromatic radicals are those with up to 14 carbon atoms; in particular there may be mentioned: phenyl, and naphthyl.

Suitable heterocyclic aromatic radicals are 5 and 6-membered heterocyclic compounds to which carbocyclic and heterocyclic radicals may be anellated. Suitable hetero atoms of these heterocyclic rings are in particular nitrogen, oxygen and sulphur, the heterocyclic rings containing one or several, the same or different hetero atoms. There may be mentioned by way of example: thienyl, pyridyl, thiazolyl.

Suitable halogens are fluorine, chlorine, bromine, iodine, preferably chlorine.

Suitable substituents of the optionally substituted radical R¹ are halogen (fluorine, chlorine, bromine, iodine), preferably chlorine, lower alkyl, halogenoalkyl and alkyoxy radicals, the nitro and hydroxy group.

Suitable lower alkyl radicals and alkyl groups of the aforementioned halogeno-alkyl and alkoxy radicals are straight-chain and branched alkyl radicals with up to 12, preferably up to 6 and in particular up to 3 carbon atoms; by way of example there may be mentioned: methyl, ethyl, propyl, isopropyl, butyl, isobutyl, tert.-butyl, amyl, isoamyl as well as the isomeric hexyl radicals.

In general, the reaction according to the invention is carried out in the presence of a solvent; as such there may be mentioned: lower aliphatic alcohols, such as ethanol, methanol, propanol, isopropanol.

Suitable β-halogeno-ethyl-aryl-ketones which may be used in the process according to the invention, are for example:
β-halogeno-ethyl-phenyl-ketone
β-halogeno-ethyl-(p-chloro-phenyl)-ketone
β-halogeno-ethyl-(p-methyl-phenyl)-ketone
β-halogeno-ethyl-(p-isopropyl-phenyl)-ketone
β-halogeno-ethyl-(p-methoxy-phenyl)-ketone
β-halogeno-ethyl-(p-oxy-phenyl)-ketone
β-halogeno-ethyl-(p-nitro-phenyl)-ketone
β-halogeno-ethyl-(dichloro-phenyl)-ketone
β-halogeno-ethyl-(2,4,6-trimethyl-phenyl)-ketone
β-halogeno-ethyl-naphthyl-ketone
β-halogeno-ethyl-thienyl-ketone Suitable thioureas, which may be used in the process according to the invention, are for example: thioureas such as
N-methyl-thiourea
N-ethyl-thiourea
N-phenyl-thiourea
N-naphthyl-thiourea
N-allyl-thiourea The reaction of β-chloro-ethyl-phenyl-ketone which can be represented by the following equation

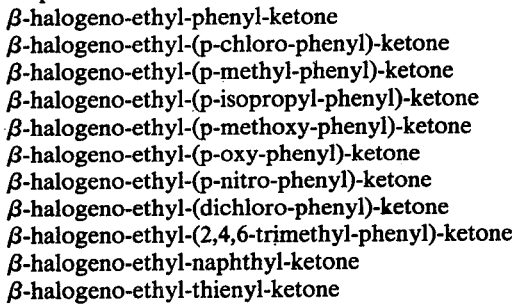

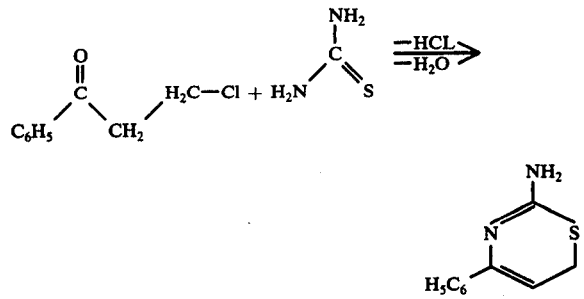

It is thought that the reaction according to the invention proceeds via non-isolated intermediate stages. An isothiuronium salt may form in the first stage with the splitting off of hydrogen chloride. In a second reaction stage the salt can then undergo cyclization to form the corresponding hydroxy-dihydro-1,3-thiazine from which water is eliminated to yield 1,3-thiazine of the formula I.

In general, performance of the process according to the invention will depend on which type of β-halogeno-ethyl-ketone of the formula II is to be used.

The selected β-halogeno-ethyl-phenyl-ketone of the formula II can for example be heated under reflux with the thiourea of the formula III in the selected solvent until starting compounds of the formula II or III are no longer detectable by the usual methods of analysis, for example, thin-layer chromatography. The reaction product may thereby precipitate in the form of its salt of halogen hydracid and can then be isolated in the normal way, e.g. by filtration. However, it is possible, preferably when the reaction product is soluble in the selected solvent, to distil the solvent off. The reaction product is then obtained as residue in the form of its salt of hydrochloric acid generally due to the alkalinity of the amino group. Using the usual methods the 2-amino-1,3-thiazine is then easily obtainable in the form of its free base. For example, the free base can be precipitated from the aqueous solution of the salt of halogen hydracid with dilute aqueous alkali metal solution and thereafter filtered. Naturally, the free base and the salt of halogen hydracid can be purified according to usual methods, for example by recrystallization. The ways and means of isolating and purifying the compounds of the invention are not essential to the invention and may proceed according to all the usual methods known in the art.

Depending on the reactivity of the selected β-halogenoethyl-ketone of the formula II, however, it may prove expedient to dissolve hydrogen chloride in the solvent being used. The amount of hydrogen chloride dissolved is not essential to the invention; it is preferably selected so that the point is not exceeded at which hydrogen chloride dissolves in the solvent at boiling temperature.

It is thought that depending on the reactivity of the initial and intermediate compounds a higher hydrogen halide concentration must prevail in the reaction mixture than results from the splitting off of hydrogen halide during the reaction in order to influence the reaction equilibrium in the right direction.

It would appear in many cases that the elimination of water from the hypothetical hydroxy-dihydro-1,3-thiazine intermediate stage only proceeds up to a state of equilibrium where the reaction medium still contains water. Thus, it may prove advantageous to remove the water from the reaction mixture in order to complete the reaction. It is expedient to remove the water as well as optionally the solvent employed, such as a lower aliphatic alcohol, by performing azeotropic distillation with a suitable solvent, which is immiscible with water, such as an aliphatic or aromatic hydrocarbon, e.g. toluene.

The stability of the new derivatives of 2-amino-1,3-thiazine varies depending on their type of substitution. In general, they are obtainable in the usual way from their salts of hydrochloric acid as free bases; however, they are often obtained as an oil and can only be purified by distillation at great loss due to their thermal instability. Even if the free base, which has separated out of the aqueous solution in the form of an oil, is extracted with an organic solvent, a pure product is often not obtained; depending apparently on the type of substitution, they may be unstable in the presence of aqueous alkaline solutions. The halogen hydracid salts however are usually the most stable and effective forms of the compounds of the invention.

The derivatives of 2-amino-1,3-thiazine, which can be obtained in accordance with the process of the invention, preferably correspond to the formula

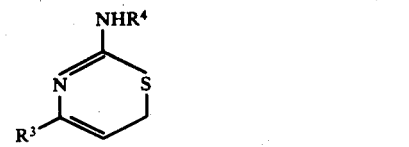

wherein
- $R^3$ represents an optionally substituted phenyl radical, naphthyl radical or thienyl radical and
- $R^4$ represents hydrogen, an alkyl radical or alkenyl radical with up to 3 carbon atoms or an optionally substituted phenyl radical or naphthyl radical.

Particularly preferred new derivatives of 2-amino-1,3-thiazine correspond to the formula

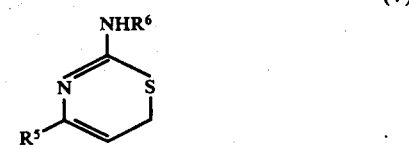

wherein
- $R^5$ represents an optionally substituted phenyl radical, naphthyl radical or thienyl radical and
- $R^6$ represents hydrogen, methyl, allyl, phenyl or naphthyl.

The new derivatives of 2-amino-1,3-thiazine possess pronounced fungitoxic and bacteriotoxic activity. They, however, have low toxicity to warm-blooded animals and do not harm crop plants in the concentrations required to combat fungi and bacteria. For these reasons they are suitable for use as plant protection agents for combating fungi and bacteria.

Fungitoxic agents are employed in plant protection for combating archimycetes, phycomycetes, ascomycetes, basidiomycetes and Fungi imperfecti.

The new compounds have a broad spectrum of activity and can be used with advantage parasitic fungi and bacteria on above-ground parts of plants or against fungi and bacteria which attack plants through the soil as well as seed-borne pathogens. In particular, the new compounds have proved particularly effective for combating bacterial diseases or bacteria which cause plant diseases. Thus, they are effective against *Xanthomonas oryzae* in rice. The new compounds are effective when applied to leaves; they also display systemic activity which is clearly in evidence after application to irrigation water or the soil. The new compounds are effective not only against *Xanthomonas oryzae* but also against bacterial pathogens of the genus Xanthomonas, Pseudomonas, Erwinia and Coryne bacterium. There may be mentioned by way of example:

Xanthomonas vesicatoria / tomatoes
Xanthomonas malvacearum / cotton
Pseudomonas lachrymans / cucumbers
Pseudomonas morsprunorum / stone fruit
Erwinia amylovora / pears and other host plants
Erwinia carotovora / on different host plants
Coryne bacterium michiganense / tomatoes.

The new compounds are likewise effective against different kinds of fungi which cause plant diseases on crop plants, e.g.: *Pyricularia oryzae, Pellicularia sasakii, Mycosphaerella musicola, Colletotrichum doffeanum, Rhizoctonia solani, Phytophthora cactorum, Phytophthora infestans, Pythium ultimum, Helminthosporium gramineum, Fusarium culmorum, Venturia inaequalis, Puccinia recondita.*

Depending on the purpose for which they are to be used, the novel compounds can be converted into the usual formulations, such as solutions, emulsions, suspensions, powders, pastes and granulates. These are produced in known manner, for example by mixing the active compounds with extenders, that is, liquid solvents, and/or solid carriers, optionally with the use of surface-active agents, that is, emulsifying agents and/or dispersing agents. In the case of the use of water as an extender, organic solvents can, for example, be used as auxiliary solvents. As liquid solvents, there are suitable: aromatics, such as xylene, toluene, chlorinated aromatics, such as chlorobenzenes, paraffins, for example mineral oil fractions, alcohols, such as methanol, butanol, strongly polar solvents, such as dimethylformamide and dimethylsulphoxide, as well as water; as solid carriers: ground natural minerals, such as kaolins, clays, talc, chalk, and ground synthetic minerals, such as highly-dispersed silicic acid, silicates; as emulsifying agents: non-ionic and anionic emulsifiers, such as polyoxyethylene-fatty acid esters, polyoxyethylene-fatty alcohol ethers, for example, alkylaryl polyglycol ethers, alkyl sulphonates, and aryl sulphonates; as dispersing agents: for example lignin, sulphite waste liquors and methyl-cellulose.

The novel compounds can be present in the formulations as a mixture with other known active compounds.

The formulations in general contain between 0.1 and 95% by weight of active compound, preferably between 0.5 and 90% by weight.

The active compounds can be used as such, in the form of their formulations or in the use forms prepared therefrom, such as ready-to-use solutions, emulsifiable concentrates, emulsions, suspensions, dispersible powders, pastes, soluble powders, dusting agents and granules. They are used in the customary manner, for example by squirting, spraying, atomising, dusting, scattering, fumigation, vaporisation, watering, dressing or incrustation.

The active compound concentrations in the ready-to-use preparations can be varied within a substantial range. In general, concentrations of 0.0001 to 10, preferably of 0.01 to 0.1%, are used.

In general, the amounts of active ingredient required for seed dressing range from 0.1 to 10 g per kilogram of seed, preferably 0.5 to 5 g per kilogram of seed. The active ingredients can also be used with success in the ultra-low-volume process (ULV) in which it is possible to apply formulations containing up to 95% or even 100% active ingredient alone.

As they are highly effective against micro-organisms such as mould fungi, yeast, bacteria, slime organisms, and algae, the new compounds can be used for the protection of materials of various types. They are versatile in their application, wherever unwanted microbial attack may be expected, for example in industrial wash-waters and cooling waters, cooling lubricants, pulp channels in paper factories, spinning baths used in synthetic fibre production, electrophoresis baths used for immersion lacquering, polymer dispersions, paper coating compositions glues, wax emulsions, dye suspensions, vegetable tanning liquids, oil-based or glue-based dye formulations, and the surfaces of skins, leather and textiles.

The quantities of substances according to the invention required for combating the micro-organisms can easily be determined by preliminary tests. They are generally in the range of from 0.0001 to 0.5% by weight, preferably 0.01 to 0.3% by weight, when used as preservatives in casks or when used as preservatives for cooling lubricants, spinning preparations, wax emulsions, filler suspensions, and spreadcoating compositions; in the range of 0.0001 to 0.01% by weight when used to combat algae and slime, for example in industrial wash-waters and cooling waters and aqueous suspensions of paper material.

Microbicidal agents based on the new compounds, which can be used in plant protection as well as for the protection of materials of various types, can be prepared in form of solutions, suspensions, pastes, dust or granulates; they may contain the active ingredient or a mixture of active ingredients as well as suitable solvents or diluents, extenders, emulsifying auxiliaries and other additives.

The following examples serve to illustrate how highly effective the new compounds are.

| Example A |
|---|
| Mycelium growth test |
| Nutrient medium used: |
| 20 parts by weight of agar-agar |
| 200 parts by weight of potato decoction |
| 5 parts by weight of malt |
| 15 parts by weight of dextrose |
| 5 parts by weight of peptone |
| 2 parts by weight of $Na_2HPO_4$ |
| 0.3 parts by weight of $Ca(NO_3)_2$ |
| and a solvent mixture of the following composition |
| 0.19 parts by weight of dimethyl formamide |
| 0.01 parts by weight of alkylarylpolyglycol ether |
| 1.80 parts by weight of water |
| 2.00 parts by weight of solvent mixture. |
| Proportion of solvent mixture to nutrient medium: |
| 2 parts by weight solvent mixture |
| 100 parts by weight agar nutrient medium |

The amount of active compound required for the desired concentration of active compound in the nutrient medium is mixed with the stated amount of solvent mixture. The concentrate is thoroughly mixed, in the stated proportion, with the liquid nutrient medium which has been cooled to 42° C and is then poured into Petri dishes of 9 cm diameter. Control dishes to which the preparation has not been added are also set up.

When the nutrient medium has cooled and solidified, the dishes are inoculated with the species of fungi stated in the table and incubated at about 21° C.

The results are evaluated after 4 to 10 days depending on the rate of growth of the fungi. Comparison is made between the radial mycelium growth on the treated culture medium and growth on the control culture medium. The stages of fungi growth are classified as follows

|   |   |
|---|---|
|   | (1) no fungi growth |
| up to | (3) very pronounced inhibition of growth |
| up to | (5) moderate inhibition of growth |
| up to | (7) weak inhibition of growth |
|   | (9) growth as in untreated control. |

Active ingredients, the concentrations of active ingredients, and the results can be seen from Table 1:

Table I

| active compounds | Active compound concentration ppm | Fusarium culmorum | Colletotrichum coffeanum | Rhizoctonia solani | Pythium ultimum | Pyricularia oryzae | Helminthosporium gramineum | Mycosphaerella musicola | Phytophthora cactorum | Pellicularia sasakii | Xanthomonas oryzae |
|---|---|---|---|---|---|---|---|---|---|---|---|
| CH₂—NH—CS—S\\Zn / CH₂—NH—CS—S (known) | 10 | 9 | 9 | 9 | 5 | 9 | 5 | 5 | 9 | 9 | 9 |
| (phenyl, NH₂/N/S·HCl) | 10 | 3 | 5 | 1 | 3 | 3 | 3 | — | 1 | 1 | 1 |
| (2,4-dichlorophenyl, NH₂/N/S·HCl) | 10 | — | — | 5 | — | 5 | — | 5 | 3 | 1 | — |
| (4-methylphenyl, NH₂/N/S·HCl) | 10 | 1 | 1 | 1 | 1 | 1 | 1 | 5 | 5 | 1 | 1 |
| (4-chlorophenyl, NH₂/N/S·HCl) | 10 | 3 | 1 | 1 | 3 | 1 | 1 | 5 | 1 | 1 | 1 |
| (4-isopropylphenyl, NH₂/N/S·HCl) | 10 | 1 | 1 | 1 | 3 | 1 | 1 | — | 1 | 1 | 1 |
| (naphthyl, NH₂/N/S·HCl) | 10 | ± | 5 | 1 | 5 | 1 | 5 | — | 1 | 1 | — |
| (thienyl, NH₂/N/S·HCl) | 10 | 1 | 1 | 1 | 1 | 1 | 1 | — | 1 | 1 | 1 |

Table I-continued

| active compounds | Active compound concentration ppm | Fusarium culmorum | Colletotrichum coffeanum | Rhizoctonia solani | Pythium ultimum | Pyricularia oryzae | Helminthosporium gramineum | Mycosphaerella musicola | Phytophthora cactorum | Pellicularia sasakii | Xanthomonas oryzae |
|---|---|---|---|---|---|---|---|---|---|---|---|
| [4-methylphenyl / phenylamino-thiazoline structure · HCl] | 10 | — | — | 5 | 5 | 3 | 3 | — | 1 | 1 | — |
| [4-methylphenyl / allylamino-thiazoline structure · HCl] | 10 | 1 | 1 | 1 | 1 | 1 | 1 | — | 1 | 1 | 1 |
| [4-methylphenyl / allylamino-thiazoline structure · HCl] | 10 | 1 | 3 | 1 | 1 | 1 | 1 | 5 | 3 | 1 | — |

EXAMPLE B

Bacteria test / Xanthomonas oryzae / Systemic 2.5 g of pumice granulate which measures 0.5 to 1 cm in diameter and contains 3 or 6% by weight of active ingredient, are introduced into the irrigation water of 6 week old rice plants which were grown in a pot, each pot containing 1500 cubic cm of soil and 1500 cubic cm of irrigation water. 2 to 3 pots were employed in each series of experiments.

The test preparations are absorbed by the roots. Two days after application of the preparation, the plants are inoculated by pricking the leaves with needles which had been previously dipped in an aqueous bacterial suspension of Xanthomonas oryzae. After inoculation the plants are left to stand in a room at 26° to 28° C and 80% relative humidity.

10 days after inoculation, the degree of infection is determined for all plants treated with the active ingredient, the leaves of which had been injured and therefore inoculated, and expressed as a percentage of untreated but likewise inoculated control plants.

0% means no infection, 100% means that the injection is exactly as great as in the case of the control plants.

Active compounds, concentrations of active compounds and the results can be seen from the following Table II:

Table II

Bacteria-test / Xanthomonas oryzae / systemic

| Active Compound | Infection in % of the infection of the untreated control at an active compound concentration (in %) of granulate | |
|---|---|---|
| | 6 % | 3 % |
| [4-isopropylphenyl thiazoline-NH₂ · HCl structure] | 67 | — |
| [naphthyl thiazoline-NH₂ · HCl structure] | 13 | — |

Table II-continued

Bacteria-test / Xanthomonas oryzae / systemic

| Active Compound | Infection in % of the infection of the untreated control at an active compound concentration (in %) of granulate | |
|---|---|---|
| | 6 % | 3 % |
| 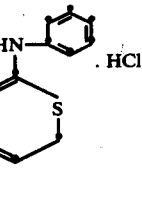 | 50 | — |
| 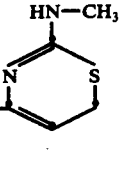 | 25 | — |
| 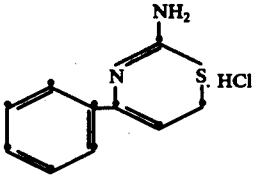 | 38 | 50 |
| 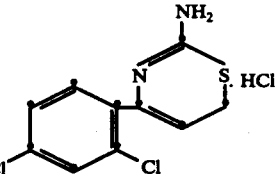 | 25 | 38 |
|  | 25 | 75 |
| 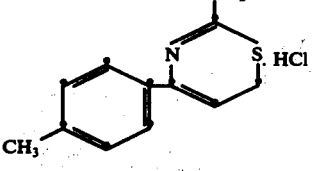 | 25 | 50 |

EXAMPLE C

In serial tests, 100 ml batches of Allen's nutrient solution, which additionally contained 1% by weight of caprolactam as the source of organic carbon and nitrogen, were admixed with the compounds given in Table III in the form of their hydrochlorides dissolved in aqueous ethanol; amounts were employed sufficient to yield concentration series between 1 and 100 mg per liter.

Shortly before adding the new compounds, the samples were infected with slime organisms (approx. 10⁶ organisms per ml) which have been isolated from the circulating spinning water employed in the production of polyamide.

The following Table III indicates the microbiostatic minimum concentration (MMC) for the hydrochlorides of the new compounds.

Solutions which contain the microbiostatic minimum concentration (MMC) or larger concentrations of active substance are still completely clear even after 3 weeks' culture at room temperature, i.e. vigorous growth of micro-organisms and formation of slime which can be seen after 3 to 4 days in nutrient solutions untreated with active substance, is suppressed. The same is true for solutions which contain a higher concentration of active substance than the microbiostatic minimum concentration (MMC). Micro-organisms do not multiply in solutions with a lower concentration of active substance than the MMC to the extent evident in nutrient solutions without any active substance; nevertheless the solutions do not remain completely clear.

The MMC values thus determined for the given compounds are set forth in Table III:

Table III

| Test organisms compound | Slime-forming caprolactam consumers MMC (mg/l) |
|---|---|
| 2-amino-4-phenyl-1,3-thiazine | 7 |
| 2-amino-4-(p-chlorophenyl)-1,3-thiazine | 7 |
| 2-amino-4-(2,4-dichlorophenyl)-1,3-thiazine | 50 |
| 2-amino-4-(p-methylphenyl) -1,3-thiazine | 15 |
| 2-amino-4-(p-isopropylphenyl) -1,3-thiazine | 30 |
| 2-amino-4-naphthyl-1,3-thiazine | 50 |
| 2-amino-4-thienyl-1,3-thiazine | 2 |
| 2-methylamino-4-(p-methylphenyl)- 1,3-thiazine | 3 |
| 2-allylamino-4-(p-methylphenyl)- 1,3-thiazine | 3 |
| 2-phenylamino-4-(p-methylphenyl)- 1,3-thiazine | 5 |

EXAMPLE D

The compounds given in Table IV were incorporated in concentrations graded from 0.005 to 0.5% by weight per test sample into an agar produced from beer wort and peptone. After the agar has solidified, the agar samples thus prepared each with a different active ingredient in a different concentration were contaminated with pure cultures of Penicillium glaucum, Chaetomicum globosum and Aspergillus niger.

The results were evaluated after 2 weeks' storage at 28° C and 60 to 70% relative humidity. The following Table gives as the MMC value the lowest concentration of active compound contained in an agar sample at which there is no growth of the particular type of microbe used on the agar sample.

Table IV

| compound | MMC (% by weight) | | |
|---|---|---|---|
| | Penicillium glaucum | Chaetomium globosum | Aspergillus niger |
| 2-amino-4-phenyl-1,3-thiazine | 0,05 | 0,01 | 0,05 |
| 2-amino-4-(p-chlorophenyl)-1,3-thiazine | 0,05 | 0,02 | 0,05 |
| 2-amino-4-(2,4-dichlorophenyl)-1,3-thiazine | 0,2 | 0,1 | 0,2 |
| 2-amino-4-(p-methylphenyl)-1,3-thiazine | 0,05 | 0,02 | 0,05 |
| 2-amino-4-(p-isopropylphenyl)-1,3-thiazine | 0,1 | 0,05 | 0,2 |
| 2-amino-4-naphthyl-1,3-thiazine | 0,5 | 0,05 | 0,5 |
| 2-amino-4-thienyl-1,3-thiazine | 0,02 | 0,005 | 0,02 |
| 2-methylamino-4-(p-methylphenyl)-1,3-thiazine | 0,05 | 0,01 | 0,03 |
| 2-allylamino-4-(p-methylphenyl)-1,3-thiazine | 0,05 | 0,01 | 0,05 |
| 2-phenylamino-4-(p-methylphenyl)-1,3-thiazine | 0,5 | 0,05 | 0,5 |

EXAMPLE E

In a manner analogous to Example D, samples were prepared with graded contents of the compounds of a bouillon agar which were given in Example D. They were then contaminated with Bacterium coli and Bacterium pyocyaneum, incubated and the results evaluated after two weeks.

The results are set forth in Table V as for Example D.

Table V

| Test organisms: bacteria | MMC (% by weight) | |
|---|---|---|
| Compound | Bacterium coli | Bacterium pyocyaneum |
| 2-amino-4-phenyl-1,3-thiazine | 0,05 | 0,1 |
| 2-amino-4-(p-chlorophenyl)-1,3-thiazine | 0,07 | 0,2 |
| 2-amino-4-(2,4-dichlorophenyl)-1,3-thiazine | 0,07 | 0,5 |
| 2-amino-4-(p-methylphenyl)-1,3-thiazine | 0,05 | 0,1 |
| 2-amino-4-naphthyl-1,3-thiazine | 0,05 | 0,5 |
| 2-amino-4-thienyl-1,3-thiazine | 0,05 | 0,1 |
| 2-methylamino-4-(p-methylphenyl)-1,3-thiazine | 0,05 | 0,2 |
| 2-allylamino-4-(p-methylphenyl)-1,3-thiazine | 0,05 | 0,2 |

EXAMPLE F

A mixed culture of green, blue, brown and silica algae is introduced into 100 ml samples of Allen's nutrient solution through which air is bubbled (Arch. Mikrobiol. 17, pages 34 – 53 (1952)). After two weeks, the nutrient solution has turned a deep greenish blue due to vigorous growth of algae.

Table VI indicates the minimum concentrations which must be reached in the solution by the addition of the given compounds in order to destroy this mixed culture of algae; activity is shown when the solution becomes colourless.

Table VI

| Concentration in % of compounds according to the invention which destroy a mixed culture of algae. | |
|---|---|
| Compound | concentration |
| 2-amino-4-phenyl-1,3-thiazine | 0,01 |
| 2-amino-4-(p-chlorophenyl)-1,3-thiazine | 0,007 |
| 2-amino-4-(2,4-dichlorophenyl)-1,3-thiazine | 0,01 |
| 2-amino-4-(p-methylphenyl)-1,3-thiazine | 0,007 |
| 2-amino-4-thienyl-1,3-thiazine | 0,005 |
| 2-methylamino-4-(p-methylphenyl)-1,3-thiazine | 0,007 |
| 2-allylamino-4-(p-methylphenyl)-1,3-thiazine | 0,005 |
| 2-phenylamino-4-(p-methylphenyl)-1,3-thiazine | 0,01 |

EXAMPLE G

In a sample of backwater from a paper factory which contains $1.5 \cdot 10^7$ micro-organisms per ml (mainly slime-forming micro-organisms) an addition of 80 ppm of 2-amino-4-(p-chlorophenyl)-1,3-thiazine reduced the number of micro-organisms by more than 99% within about 5 hours.

EXAMPLE H

The preservation of plasticizer-containing emulsion paints is particularly fraught with difficulty. Relatively high concentrations of the known preservation agent are required to attain sufficient stability in storage.

Samples of such an emulsion paint with a content of 0.15 and 0.2% by weight of 2-amino-4-thienyl-1,3-thiazine were infected with micro-organisms isolated from decayed emulsion paint. All microbial decomposition was suppressed; bacterial counts showed that the micro-organisms introduced had been killed.

EXAMPLE 1

20.3 g (0.1 mol) of $\beta$-chloroethyl-phenyl ketone together with 7.6 g (0.1 mol) of thiourea in 100 ml of ethanol in which 0.5% by weight of hydrogen chloride is dissolved, are heated to the boil (for about 3 to 4 hours) until the starting compounds can no longer be detected in a sample by thin-layer chromatography. Thereafter ethanol is azeotropically distilled off whilst toluene is continuously added in the same amount as ethanol distils off and the resulting toluene reaction mixture is boiled for a further ¼ hour on the water separator. 23 g (about 88% of the theory) of crude 2-amino-4-phenyl-1,3-thiazine hydrochloride (m.p. 204° C) separate out as faintly yellow-coloured crystals and are filtered off. By recrystallizing from ethanol, pure 2-amino-4-phenyl-1,3-thiazine-hydrochloride is obtained with a melting point of 210° C.

Analysis: $C_{10}H_{11}ClN_2S$ (Mol 226,7); % calculated for: C 53,0 H 4,82 N 12,35 Cl 15,65 S 14.18. % found: C 53,0 H 4,52 N 12,3 Cl 15,7 S 14,3.

The free base is precipitated and filtered off from the aqueous solution of the hydrochloride by adding dilute aqueous sodium hydroxide solution. Pure 2-amino-4-phenyl-1,3-thiazine with a melting point of 137° C is obtained by recrystallising from a mixture containing the same parts by volume of benzene and cyclohexane.

Analysis: $C_{10}H_{10}N_2S$ (Mol 190,27). % calulated for: C 63,1 H 5,25 N 14,7 S 16,85. % found: C 63,0 H 5,36 N 14,4 S 16,5.

EXAMPLES 2 – 6

As described in Example 1, 0.1 mol of thiourea was reacted with 0.1 mol of a $\beta$-chloro ethyl ketone of the formula $$R^3 - CO - CH_2 - CH_2 - Cl \qquad (IV)$$

wherein $R^3$ has the meaning given in Table VII, in 100 ml of ethanol which contains 0.5% by weight of dissolved hydrogen chloride.

The resultant compounds and their melting points are set forth in Table VII.

Table VII

| Ex. No. | $R^3$ | New compound | melting point Hydro-chloride | yield |
|---|---|---|---|---|
| 2 | p-chlorophenyl | 2-amino-4-(p-chlorophenyl)-1,3-thiazine | 223° C | 88.5% of the theory |
| 3 | p-methylphenyl | 2-amino-4-(p-methylphenyl)-1,3-thiazine | 211° C | 98.5% of the theory |
| 4 | p-isopropyl-phenyl | 2-amino-4-(p-isopropylphenyl)-1,3-thiazine | 213° C | 98 % of the theory |
| 5 | thienyl | 2-amino-4-thienyl-1,3-thiazine | 192° C | 98 % of the theory |
| 6 | naphthyl-(2) | 2-amino-4-naphthyl-(2)-1,3-thiazine | 210° C | 73.5% of the theory |

The free base of the compound given in Example 2 has a melting point of 127° C.

EXAMPLE 7

2.9g (0.025 mol) of N-allyl thiourea and 4.7 g (0.025 mol) of p-methylphenyl-β-chloro-ethyl ketone are heated under reflux for half an hour in 100 ml of ethanol, which contains 0.5% by weight of dissolved hydrogen chloride. Thereafter evaporation to dryness is carried out in the waterpump vacuum at about 45° C bath temperature in the waterbath whilst adding toluene a number of times. The residue is taken up in about 30 ml of acetone. After trituration with a little ether, 6.3 g (approximately 90% of the theory) of 2-allylamino-4-(p-methylphenyl)-1,3-thiazine-hydrochloride precipitate from the acetone solution as crystals. The compound is obtained in pure form by recrystallising from acetone; melting point 133° C.

Analysis: $C_{14}H_{17}ClN_2$ (mol 280.81). % calculated for: C 59.90 H 6.09 N 9.96 S 11,4 Cl 12.65. % found: C 60.0 H 6.06 N 9.99 S 11,3 Cl 12,6.

EXAMPLE 8

3.8 g (0.025 mol) of N-phenyl thiourea and 4.7 g (0.025 mol) of p-methylphenyl-β-chloro-ethyl-ketone are heated for one hour under reflux in 100 ml of ethanol, which contains 0.5% by weight of dissolved hydrogen chloride. The reaction mixture is then worked up as described in Example 2. 5.7 g (approximately 71% of the theory) of 2-phenyl-amino-4-(p-methylphenyl)-1,3-thiazine-hydrochloride are obtained with a melting point of 179° C after recrystallising from a mixture of the same parts by volume of acetone and methanol.

EXAMPLE 9

24.0 g (0.1 mol) of 2.4-dichloro-phenyl-β-chloroethylketone (95%) are heated under reflux with 7.6 g (0.1 mol) of thiourea in 100 ml of ethanol. After approximately 3.5 hours, the reaction product has separated off as colourless crystals; 23.7 g (approximately 85% of the theory) of 2-amino-4-(2,4-dichloro-phenyl)-1,3-thiazine-hydrochloride are obtained as colourless crystals with a melting point of 236° C.

Analysis: $C_{10}H_9Cl_3N_2S$ (Mol 259,62). % Calculated for: C 40,64 H 3,08 N 9,43 S 10,8 Cl 36,05. % found: C 40,7 H 3,08 N 9,29 S 11,0 Cl 36,1.

Upon adding dilute aqueous sodium hydroxide solution to an aqueous solution of the hydrochloride the base separates off as a white precipitate; by recrystallising from benzine 2-amino-4-(2,4-dichlorophenyl)-1,3-thiazine is obtained with a m.p. of 166° C.

Analysis: $C_{10}H_8Cl_2N_2S$ (Mol 259,17). % calculated for: C 46,60 H 3,15 N 10,81 S 11,94 Cl 27,5. % found: C 46,3 H 3,28 N 10,9 S 11,6 Cl 27,9.

EXAMPLE 10

4.7 g (0.025 mol) of β-chloro-ethyl-(p-methylphenyl)-ketone are heated to the boil for about 30 minutes with 2.25 g (0.025 mol) of N-methyl-thiourea in 100 ml of ethanol, which contains 0.5% by weight of hydrogen chloride, until the starting compounds can no longer be detected in a sample taken from reaction mixture by thin-layer chromatography. The ethanol is distilled off from the reaction solution and simultaneously replaced by toluene and the resulting toluene solution boiled for about half an hour on the water separator. 5.6 g (approximately 86% of the theory) of 2-methylamino-4-(p-methylphenyl)-1,3-thiazinehydrochloride separate off as brown, tacky crystals. The melting point of the pure compound is 162° C after recrystallising from acetone / methanol (2:1).

EXAMPLE 11

4.7 g (0.025 mol) of β-chloro-ethyl-(p-methylphenyl)-ketone are heated to the boil for about 1 hour with 5.05 g (0.025 mol) of N-naphthyl-(2)-urea in 100 ml of ethanol which contains 0.5% by weight of hydrogen chloride. The mixture is kept at this temperature (for approximately 1 hour) until the starting compounds can no longer be detected in a sample taken from the reaction mixture by thin-layer chromatography. The ethanol is then distilled off and simultaneously replaced by toluene and the resulting toluene solution boiled for a further half an hour approximately on the water separator. 6.9 g (approximately 72.7% of the theory) of 2-napht-hyl-(2)-amino-4-(p-methyl-phenyl)-1,3-thiazine-hydrochloride separate off as light-grey crystals with a melting point of 210° C. The pure compound with a melting point of 212° C is obtained by recrystallising from methanol.

What is claimed is:
1. A 2-amino-1,3-thiazine of the formula

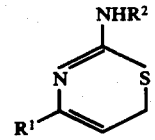

wherein
  $R^1$ is optionally substituted phenyl, naphthyl, thienyl, pyridyl or thiazolyl, and
  $R^2$ is hydrogen, alkyl or alkenyl with up to 18 carbon atoms, or optionally substituted phenyl, naphthyl, thienyl, pyridyl or thiazolyl,
  the optional substituents for $R^1$ and $R^2$ constituting up to three radicals selected from the group consisting of halogen, nitro hydroxy, or alkyl, halogeno-alkyl or alkoxy with up to 12 carbon atoms.

2. A thiazine according to claim 1, wherein
  $R^1$ is optionally substituted phenyl, naphthyl or thienyl, and
  $R^2$ is hydrogen, alkyl or alkenyl with up to 3 carbon atoms, or optionally substituted phenyl or naphthyl.

3. A thiazine according to claim 2, wherein $R^2$ is hydrogen, methyl, allyl, phenyl or naphthyl.

4. A thiazine according to claim 1, wherein such thiazine is 2-amino-4-phenyl-1,3-thiazine.

5. A thiazine according to claim 1, wherein such thiazine is 2-amino-4-(1,4-dichlorophenyl)-1,3-thiazine.

6. A thiazine according to claim 1, wherein such thiazine is 2-amino-4-(4-chlorophenyl)-1,3-thiazine.

7. A thiazine according to claim 1, wherein such thiazine is 2-amino-4-(4-isopropylphenyl)-1,3-thiazine.

8. A thiazine according to claim 1, wherein such thiazine is 2-amino-4-naphthyl-1,3-thiazine.

9. A thiazine according to claim 1, wherein such thiazine is 2-amino-4-thienyl-(2)-1,3-thiazine.

10. A thiazine according to claim 1, wherein such thiazine is 2-amino-4-(4-methylphenyl)-1,3-thiazine.

11. A thiazine according to claim 1, wherein such thiazine is 2-phenylamino-4-(4-methylphenyl)-1,3-thiazine.

12. A thiazine according to claim 1, wherein such thiazine is 2-naphthylamino-4-(4-methylphenyl)-1,3-thiazine.

13. A thiazine according to claim 1, wherein such thiazine is 2-methylamino-4-(4-methylphenyl)-1,3-thiazine.

14. A thiazine according to claim 1, wherein such thiazine is 2-allylamino-4-(4-methylphenyl)-1,3-thiazine.

15. A process for preparing a thiazine according to claim 1, which comprises reacting a beta-halogen-ethyl-ketone of the formula $$R^1-CO-CH_2-CH_2-Hal$$

wherein
Hal is halogen,
with a thiourea of the formula

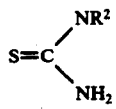

16. The process according to claim 15, wherein the reaction is effected at a temperature from 15° to 150° C.

17. The process according to claim 16, wherein the reaction is effected in the presence of a solvent.

18. The process according to claim 17, wherein hydrogen chloride is dissolved in the solvent.

19. The process according to claim 15, wherein water and optionally solvent are removed by azeotropic distillation with an aliphatic or aromatic hydrocarbon.

20. A fungicidal or bactericidal composition comprising a fungicidally or bactericidally effective amount of a thiazine in accordance with claim 1 in admixture with a diluent.

21. A method for combatting fungi or bacteria which comprises applying to such fungi, bacteria or a habitat thereof a fungicidally or bactericidally effective amount of a thiazine according to claim 1.

22. The method according to claim 21, wherein the thiazine is applied to a plant.

23. The method according to claim 21, wherein the thiazine is 2-amino-4-phenyl-1,3-thiazine.

24. The method according to claim 21, wherein the thiazine is 2-amino-4-(2,4-dichlorophenyl)-1,3-thiazine.

25. The method according to claim 21, wherein the thiazine is 2-amino-4-(4-chlorophenyl)-1,3-thiazine.

26. The method according to claim 21, wherein the thiazine is 2-amino-4-(4-isopropylphenyl)-1,3-thiazine.

27. The method according to claim 21, wherein the thiazine is 2-amino-4-naphthyl-1,3-thiazine.

28. The method according to claim 21, wherein the thiazine is 2-amino-4-thienyl-(2)-1,3-thiazine.

29. The method according to claim 21, wherein the thiazine is 2-amino-4-(4-methylphenyl)-1,3-thiazine.

30. The method according to claim 21, wherein the thiazine is 2-phenylamino-4-(4-methylphenyl)-1,3-thiazine.

31. The method according to claim 21, wherein the thiazine is 2-naphthylamino-4-(4-methylphenyl)-1,3-thiazine.

32. The method according to claim 21, wherein the thiazine is 2-methylamino-4-(4-methylphenyl)-1,3-thiazine.

33. The method according to claim 21, wherein the thiazine is 2-allylamino-4-(4-methylphenyl)-1,3-thiazine.

* * * * *